United States Patent [19]

Reifschneider et al.

[11] Patent Number: 4,950,657
[45] Date of Patent: Aug. 21, 1990

[54] ((1-PIPERAZINYL)CARBONYL)PHOSPHORAMIDOTHIOATE ESTER INSECTICIDES

[75] Inventors: Walter Reifschneider, Walnut Creek; Barat Bisabri-Ershadi, Davis; James E. Dripps, Concord; J. Brian Barron, Benicia, all of Calif.

[73] Assignee: The Dow Chemical Company, Midland, Mich.

[21] Appl. No.: 420,083

[22] Filed: Oct. 10, 1989

[51] Int. Cl.$^5$ ................ A01N 57/32; C07F 9/6509
[52] U.S. Cl. .................................. 514/85; 544/232; 558/178
[58] Field of Search ................. 514/85; 544/232

[56] References Cited

U.S. PATENT DOCUMENTS 4,225,595  9/1980  Fancher ........................... 514/85

OTHER PUBLICATIONS

Derkach et al., *Zh. Obshch. Khim.*, 39, 1549–1552 (1963) (English translation).
Samarai et al., *Zh. Obshch. Khim.*, 39, 1480–1482 (1969) (English translation).
Derkach et al., *Zh. Obshch. Khmi.*, 34, 3096–3098 (1964) (English translation).
Mel'nikov et al., (Chemical Abstracts, 87, 183905n (1977)).
Kristiansen et al., Chemical Abstracts, vol. 89, No. 179559 (1978), (Abstract for DE 2805682, 8/17/78).
Kristiansen et al., Chemical Abstracts, vol. 88, No. 70501 (1978), (Abstract for DE 2718554, 11/10/77).

*Primary Examiner*—Mukund J. Shah
*Assistant Examiner*—E. Bernhardt
*Attorney, Agent, or Firm*—D. Wendell Osborne

[57] ABSTRACT

O,S-Dialkyl ((piperazinyl)carbonyl)phosphoramidothioates are prepared by the reaction of O,S-dialkyl phosphoroisocyanatidothioates with substituted piperazines and found to be effective plant systemic and contact insecticides. ((4-(1,1-Dimethylethyl)-1-piperazinyl)carbonyl)phosphoramidothioate, for example, is prepared from O,S-dimethyl phosphoroisocyanatidothioate and 4-(1,1-dimethylethyl)piperazine and found to control aster leafhoppers when applied to rice plants.

30 Claims, No Drawings

((1-PIPERAZINYL)CARBONYL)PHOSPHORAMIDOTHIOATE ESTER INSECTICIDES

BACKGROUND OF THE INVENTION

The present invention relates to O,S-dialkyl heterocyclylcarbonylphosphoramidothioates derived from substituted piperazines, which can be named ((1-piperazinyl)carbonyl)phosphoramidothioate esters, to insecticidal compositions containing the compounds, and to the use of the compounds as insecticides.

The control of insects is critical to modern agriculture and to the maintenance of public health. Although many compounds that are useful in the control of insects are known, new compounds that are more effective, are less toxic to mammals, are more compatible with the environment, are less expensive, or have other outstanding properties, are constantly sought and when found highly valued.

Many of the compounds known to be useful in the control of insects are organophosphorus compounds. Such compounds include O,S-dimethyl phosphoramidothioate (methamidophos) and O,S-dimethyl acetylphosphoramidothioate (acephate). Certain O,S-dialkyl N,N-dialkylcarbamoylphosphoramidothioates and their use as insecticides is disclosed in published German Patent Applications 2,718,554, and 2,805,682. The use of these known compounds as insecticides is often limited due to their toxicological and environmental properties, their lack of persistence, and their lack of activity on certain important insects. Certain ((1-morpholinyl)carbonyl)phosphoramidothioate esters are also disclosed in the art (*Zh. Obshch. Khim.*, 9, 1511–1513 (1969)).

SUMMARY OF THE INVENTION

It has now been found that certain O,S-dialkyl ((1-piperazinyl)carbonyl)phosphoramidothioates, which can be viewed as O,S-dialkyl N-(substituted-carbamoyl)phosphoramidothioates in which the substituent and the nitrogen of the carbamoyl moiety form a substituted piperazine moiety, have excellent plant systemic and contact insecticidal, acaracidal, and nematicidal activity against important species, but are relatively low in mammalian and fish toxicity.

The invention includes compounds of the formula

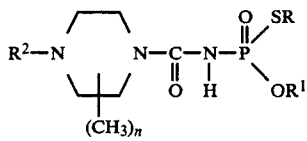

wherein
R and $R^1$ each independently represent $C_1$–$C_4$ alkyl;
$R^2$ represents H, $C_1$–$C_8$ alkyl (optionally containing up to two substituents selected from F, Cl, Br, CN, $CO_2(C_1$–$C_4$ alkyl), $C_1$–$C_4$ alkoxy, $C_1$–$C_4$ alkylthio, or phenyl), $C_3$–$C_6$ cycloalkyl, phenyl, COH, CO($C_1$–$C_4$ alkyl), COphenyl, $CO_2(C_1$–$C_4$alkyl), or CONH-P(O)(SR)($OR^1$); each phenyl optionally containing up to three substituents selected from F, Cl, Br, $CH_3$, $CF_3$, CN, $OCH_3$, $SCH_3$; and
n represents 0, 1, or 2.

Compositions containing insecticidal amounts of the compounds of the invention in admixture with at least one agriculturally acceptable adjuvant or carrier are useful for the control of insects. A wide variety of insects is controlled by application of insecticidal amounts of the compounds to the insects or to their locus or to plants that insects feed on or their locus. Both plant systemic and contact insecticidal activity are exhibited. Sucking insects, such as leafhoppers, are especially susceptible.

DETAILED DESCRIPTION OF THE INVENTION

The compounds of the invention include those O,S-dialkyl ((1-piperazinyl)carbonyl)phosphoramidothioate compounds of the formula

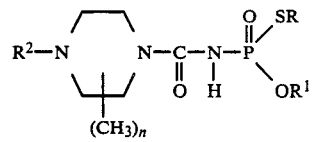

wherein
R and $R^1$ each independently represent $C_1$–$C_8$ alkyl;
$R^2$ represents H, $C_1$–$C_4$ alkyl (optionally containing up to two substituents selected from F, Cl, Br, CN, $CO_2(C_1$–$C_4$ alkyl), $C_1$–$C_4$ alkoxy, $C_1$–$C_4$, alkylthio, or phenyl), $C_3$–$C_6$ cycloalkyl, phenyl, COH, CO($C_1$–$C_4$ alkyl), COphenyl, $CO_2(C_1$–$C_4$ alkyl), or CONH-P(O)(SR)($OR^1$), each phenyl optionally containing up to three substituents selected from F, Cl, Br, $CH_3$, $CF_3$, CN, $OCH_3$, $SCH_3$; and
n represents 0, 1, or 2.

The compounds of the invention can be characterized as substituted O,S-dialkyl N-(substituted-carbamoyl)-phosphoramidothioate esters in which the substituted-carbamoyl moiety is derived from a piperazine compound which is optionally substituted on the 4-position nitrogen with one of a variety of substituents and on the 2-, 3-, 5-, and 6-position carbon atoms with methyl. The possible substituents on the 4-position nitrogen include optionally substituted alkyl, cycloalkyl, optionally substituted phenyl, formyl, acyl, alkoxycarbonyl, and ((((alkoxy)alkylthio)phosphinyl)amino)carbonyl. Suitable substituted alkyl moieties contain 1 to 8 carbon atoms in either a straight chain or a branched chain configuration and may contain one or two substituent atoms or groups, such as F, Cl, Br, CN, $CO_2(C_1$–$C_4$ alkyl), $C_1$–$C_4$ alkoxy, $C_1$–$C_4$ alkylthio, and optionally substituted phenyl. Unsubstituted $C_3$–$C_4$ alkyl, optionally substituted benzyl (phenylmethyl), optionally substituted diphenylmethyl, and CO($C_1$–$C_4$ alkyl) are often preferred. Suitable substituted phenyl moieties in each situation may contain one to three substituent atoms or groups, such as F, Cl, Br, $CH_3$, $CF_3$, CN, $OCH_3$, and $SCH_3$.

The R and $R^1$ substituents on the phosphorothioic acid moiety of the compounds of the invention are independently selected from either straight chain or branched chain $C_1$–$C_4$ alkyl groups. Methyl, ethyl, propyl, isopropyl, and isobutyl are typical. Compounds wherein both R and $R^1$ represent methyl are often preferred as are compounds wherein R represents n-propyl and $R^1$ represents ethyl.

The compounds of the present invention contain an asymmetric phosphorus atom and in some cases one or more asymmetric carbon atoms and, therefore, exist as optical isomers. The present invention relates to each of these optical isomers individually and to all mixtures thereof as well as to all geometric isomers.

The compounds of the invention include, but are not limited by, the compounds illustrated in the following table.

tion. The compounds of the invention are generally oily liquids or colorless solids.

The starting materials for the above method are generally well known in the art or can readily be prepared using the methods taught in the art. The preparation of the isocyanatidophosphoramidate esters can be conve-

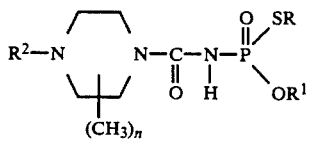

| Cpd No. | R | R¹ | R² | n | MP, °C. or RI @ 25° C. | Elem. Anal.[1] |
|---|---|---|---|---|---|---|
| 1 | $CH_3$ | $CH_3$ | H | 2(2-,6-) | 230(d) | CHN |
| 2 | $CH_3$ | $CH_3$ | $CH_3$ | 0 | 108–109 | CHN |
| 3 | $CH_3$ | $CH_3$ | $(CH_3)_2CH$ | 0 | 124–126 | CHN |
| 4 | $CH_3$ | $CH_3$ | $(CH_3)_3C$ | 0 | 133–135 | CHN |
| 5 | $CH_3$ | $CH_3$ | $C_6H_5$ | 0 | 126–128 | CHN |
| 6 | $CH_3$ | $CH_3$ | $C_6H_5CH_2$ | 0 | 124–125 | CHN |
| 7 | $CH_3$ | $CH_3$ | $4\text{-}ClC_6H_4CH_2$ | 0 | 153–153.5 | CHN |
| 8 | $CH_3$ | $CH_3$ | $(C_6H_5)_2CH$ | 0 | 124–125 | CHN |
| 9 | $CH_3$ | $CH_3$ | $(4\text{-}ClC_6H_4)_2CH$ | 0 | 181–182 | |
| 10 | $CH_3$ | $CH_3$ | HC(O) | 0 | 94–103 | HN |
| 11 | $CH_3$ | $CH_3$ | $CH_3C(O)$ | 0 | 108–111 | CHN |
| 12 | $CH_3$ | $CH_3$ | $C_2H_5O_2C$ | 0 | 114–115.5 | CHN |
| 13 | $CH_3$ | $CH_3$ | $CH_3O\text{-}P(O)NHCO\text{-}CH_3S$ | 0 | 178–180 | CHN |
| 14 | $C_3H_7$ | $C_2H_5$ | $(C_6H_5)_2CH$ | 0 | 122–124 | CHN |
| 15 | $C_3H_7$ | $C_2H_5$ | $(4\text{-}ClC_6H_4)_2CH$ | 0 | 183–184 | CHN |
| 16 | $C_3H_7$ | $C_2H_5$ | HC(O) | 0 | 1.5373 | CHN |
| 17 | $C_3H_7$ | $C_2H_5$ | $C_2H_5O_2C$ | 0 | 83–85 | CHN |

[1]Acceptable analyses obtained

The compounds of the present invention can be prepared by the reaction of an appropriate O,S-dialkyl phosphoroisocyanatidothioate and an appropriate nitrogen heterocycle as shown in the following scheme wherein all substituents are defined as above:

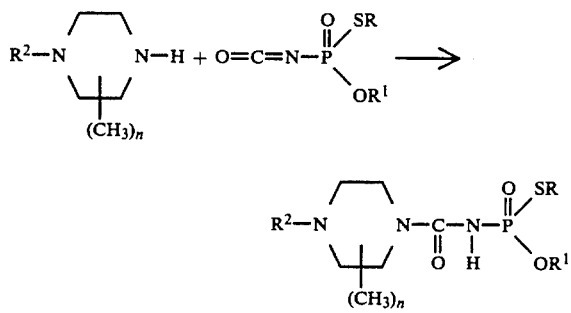

The reaction can be conducted by combining the two starting materials in a solvent, such as ether, toluene, methylene chloride, or acetonitrile at about −10° C. to about 60° C. and allowing them to react. The product, a compound of the present invention, that forms can be recovered by conventional means, such as by evaporation of the solvent or, in the case of solids, by filtration and drying. The recovered products can be purified by conventional means, such as by liquid chromatography, by extraction with solvents in which the products are poorly soluble, or, in the case of solids, by recrystallizaniently accomplished by heating an O,S-dialkyl phosphoramidothioate with phosgene or oxalyl chloride in a solvent. The 4-alkylpiperazine compounds can be prepared by alkylation of a 1-ethoxycarbonylpiperazine compound with an alkyl halide to obtain a 4-alkyl-1-ethoxycarbonylpiperazine and then removing the ethoxycarbonyl moiety by hydrolysis. Some of the 1-alkyl and 1-arylpiperazines can be prepared from the appropriate alkylamine or aniline by sequential treatment with ethylene oxide or propylene oxide, thionyl chlorine, and benzylamine to obtain a 4-alkyl or 4-aryl-1-benzylpiperazine and then removing the benzyl moiety with hydrogen and a palladium on carbon catalyst.

The compounds of the present invention can be used directly as insecticides, but it is generally preferable to first prepare an insecticidal composition containing one or more of the compounds in combination with an agriculturally acceptable adjuvant or carrier. Suitable adjuvants or carriers should not be phytotoxic to valuable crops, particularly at the concentrations employed in applying the compositions for insect control in the presence of crops, and should not react chemically with the insecticidal compounds or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the insecticidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, fungicides, other insecticides, and the like and can be formulated with solid, particulate fertilizer carriers such as ammonium nitrate, urea and the like or with liquid fertilizers.

The concentration of the active ingredients in the insecticidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to insects or their locus or to plants or their locus generally contain about 0.001 to about 0.1 weight percent active ingredient and preferably contain about 0.005 to about 0.05 percent.

The present compositions can be applied by the use of conventional ground or aerial dusters and sprayers, by addition to irrigation water, and by other conventional means known to those skilled in the art.

The compounds of the invention are useful for the control of a wide variety of insects, mites, and nematodes. Sucking and chewing insects, especially sucking insects, are susceptible to the compounds. Leafhoppers, in particular, are well controlled.

The compounds are active against insect pests by both contact and plant systemic action and, consequently, can be applied either directly to the insects or to the locus thereof so that they will come in contact with the exterior parts of the insect pest or can be applied to plants insects feed on or the locus of such plants so that they will be ingested by the insect pests. It is often preferred to apply the compounds to plants or to the locus of plants and take advantage of the plant systemic properties of the compounds. The treatment of rice plants or their locus to control leaf hoppers is a preferred application.

The following examples are presented to illustrate the invention; they should not be construed as limiting.

EXAMPLES

Example 1 - Preparation of O,S-Dimethyl ((4-(1,1-Dimethylethyl)-1-piperazinyl)carbonyl)phosphoramidothioate To a stirred solution of 2.85 grams (g) of 1-(1,1-dimethylethylpiperazine in 60 milliliters (ml) of ether was added dropwise at ambient temperature 3.4 g of O,S-dimethyl phosphoroisocyanatidothioate. A precipitate began to form almost immediately. After a short time this precipitate was collected by filtration, extracted with ether, and dried to obtain 5.34 g of the title compound (86 percent of theory) as white crystals melting at 133-135° C.

Elemental Analysis (percent): Calc for $C_{11}H_{24}N_3O_3PS$: C, 42.70; H, 7.82; N, 13.58. Found: C, 42.51; H, 7.63; N, 13.53.

Example 2 - Preparation of O,S-Dimethyl (4-Acetyl-1-piperazinyl)carbonyl)phosphoramidothioate To a solution of 2.0 g of 1-acetylpiperazine in 150 ml of dry ether was added dropwise with stirring at ambient temperature 2.9 g of O,S-dimethyl phosphoroisocyanatidothioate. A precipitate began to form almost immediately. After a short time this precipitate was collected by filtration, extracted with ether, and dried to obtain 4.4 g of the title compound (95 percent of theory) as white crystals. The crystals were recrystallized from ethanol-ether to obtain 3.2 g of purified product melting at 108°-111° C.

Elemental Analysis (percent): Calc for $C_9H18N304PS$: C, 36.61; H, 6.14; N, 14.23. Found C, 36.24; H, 6.01; N, 14.00.

Example 3 - Preparation of O,O',S,S'-Dimethyl ((2,6-Dimethyl-1,4-piperazindiyl)dicarbonyl)bisphosphoramidothioate.

To a solution of 2.3 g of 2,6-dimethylpiperazine in 50 ml of methylene chloride was added dropwise with stirring at ambient temperature 5.1 g of O,S-dimethyl phosphoroisocyanatidothioate. A precipitate began to form almost immediately. After stirring overnight the precipitate was collected by filtration and dried to obtain 8.0 g of the title compound as a white solid melting at 158°–160° C.(d).

Elemental Analysis (percent): Calc for $C_{12}H_{26}N_4O_6P_2S_2$: C, 32.1; H, 5.84; N, 12.49. Found: C, 33.5; H, 6.08; N, 12.33.

Example 4 - Preparation of O,S-Dimethyl ((2,6-Dimethyl-4-piperazinyl)carbonyl)phosphoramidothioate O,O',S,S'-Dimethyl ((2,6-dimethyl-1,4-piperazindiyl)dicarbonyl)bisphosphoramidothioate (8.0 g) was dissolved in hot methanol and allowed to react for a few minutes. The mixture was subsequently allowed to cool and ether was added. A white solid (4.1 g) precipitated. This precipitate was collected by filtration and recrystallized from methanol and ether to obtain the title compound as white crystals melting at 230° C. with decomposition.

Elemental Analysis (percent): Calc for $C_9H_{20}N_3O_3PS$: C, 38.42; H, 7.17; N, 14.94. Found: C, 38.09; H, 7.07; N, 14.62.

Example 5 - Insecticidal Activity Against Aster Leaf-Hopper

Test compounds were dissolved in a small amount of acetone and the resulting solutions were diluted with distilled water containing 0.1 percent Triton ™ X-100 surfactant (an octylphenol ethoxylate nonionic surfactant) to obtain application mixtures containing known amounts. Rice plants were grown in vermiculite in a greenhouse under controlled conditions.

Foliar treatments were made to determine the contact insecticidal activity. Individual rice plants were sprayed to runoff with an application mixture containing a known concentration of a test compound and then the plants were allowed to dry for 1 hour. Control plants were treated in the same way with a surfactant solution prepared in the same way as the application mixtures. Root treatments were made to determine the systemic insecticidal activity. Individual rice plants were transferred to an individual hydroponic system and 25 ml of an application mixture containing a known concentration of a test compound was added to the system. Control plants were treated in the same way with a surfactant solution prepared in the same way as the application mixtures.

A plastic cylinder was placed around each of the plants and 10 adult aster leafhoppers (*Macrosteles severni*) were placed in each cylinder. The cylinders were capped and maintained under conditions conducive to the growth of the plants and the insects. After two days the contents of each cylinder was examined to determine the percentage of the aster leafhoppers that were dead. The results were collected and an $LC_{50}$ (the concentration at which one half of the insects died) calculated for each compound tested. The results are given in the following table.

| CONTROL OF ASTER LEAFHOPPERS | | |
| --- | --- | --- |
| Compound Number | Contact $LC_{50}$, ppm | Systemic $LC_{50}$, ppm |
| 2 | 11 | 2.3 |
| 3 | 10.6 | 0.53 |
| 4 | 4.3 | 0.59 |
| 5 | >20 | 1.9 |
| 6 | 10.3 | 0.66 |

| CONTROL OF ASTER LEAFHOPPERS -continued | | |
| --- | --- | --- |
| Compound Number | Contact $LC_{50}$, ppm | Systemic $LC_{50}$, ppm |
| 7 | 8.4 | 0.62 |
| 8 | 10.9 | 0.25 |
| 9 | 6.3 | 0.99 |
| 10 | 14 | 1.6 |
| 11 | 6.7 | 0.71 |
| 12 | 12 | 1.8 |
| 13 | 12.5 | 0.87 |
| 14 | 10.9 | 1.2 |
| 15 | >20 | 1.6 |
| 16 | 7.5 | 1.2 |
| 17 | 20 | 0.77 |

What is claimed is:

1. A compound of the formula $$R^2-N\diagup\diagdown N-\underset{\underset{O}{\|}}{C}-\underset{\underset{H}{|}}{N}-\underset{\underset{OR^1}{}}{\overset{\overset{O}{\|}}{P}}\diagdown^{SR}$$
$$(CH_3)_n$$

wherein
R and $R^1$ each independently represent $C_1$–$C_4$ alkyl;
$R^2$ represents H, $C_1$–$C_8$ alkyl (optionally containing up to two substituents selected from F, Cl, Br, CN, $CO_2(C_1$–$C_4$ alkyl), $C_1$–$C_4$ alkoxy, $C_1$–$C_4$ alkylthio, or phenyl), $C_3$–$C_6$ cycloalkyl, phenyl, COH, CO($C_1$–$C_4$ alkyl), COpheny $CO_2(C_1$–$C_4$ alkyl), or CONH-P(O)(SR)(OR$^1$), each phenyl optionally containing up to three substituents selected from F, Cl, Br, $CH_3$, $CF_3$, CN, $OCH_3$, $SCH_3$; and
n represents 0, 1, or 2.

2. A compound of claim 1 wherein n represents zero.

3. A compound of claim 1 wherein $R^2$ represents unsubstituted $C_3$–$C_4$ alkyl, optionally substituted benzyl, optionally substituted diphenylmethyl, or CO($C_1$–$C_4$ alkyl).

4. A compound of claim 3 wherein $R^2$ represents branched chain $C_3$–$C_4$ alkyl.

5. A compound of claim 1 wherein R and $R^1$ each represent methyl.

6. A compound of claim 5, O,S-dimethyl ((4-(1,1-dimethylethyl)-1-piperazinyl)carbonyl)phosphoramidothioate.

7. A compound of claim 5, O,S-dimethyl ((4-(diphenylmethyl)-1-piperazinyl)carbonyl)phosphoramidothioate.

8. A compound of claim 5, O,S-dimethyl ((4-benzyl-1-piperazinyl)carbonyl)phosphoramidothioate.

9. A compound of claim 5, O,S-dimethyl ((4-acetyl-1-piperazinyl)carbonyl)phosphoramidothiate.

10. An insecticidal composition comprising an agriculturally acceptable adjuvant or carrier and an insecticidally effective amount of a compound of the formula $$R^2-N\diagup\diagdown N-\underset{\underset{O}{\|}}{C}-\underset{\underset{H}{|}}{N}-\underset{\underset{OR^1}{}}{\overset{\overset{O}{\|}}{P}}\diagdown^{SR}$$
$$(CH_3)_n$$

wherein

R and R$^1$ each independently represent C$_1$–C$_4$ alkyl:

R$^2$ represents H, C$_1$–C$_8$ alkyl (optionally containing up to two substituents selected from F, Cl, Br, CN, CO$_2$(C$_1$–C$_4$ alkyl), C$_1$–C$_4$ alkoxy, C$_1$–C$_4$, alkylthio, or phenyl): C$_3$–C$_6$ cycloalkyl, phenyl, COH, CO(C$_1$–C$_4$ alkyl), COphenyl, CO$_2$(C$_1$14 C$_4$ alkyl), or CONHP(O)(SR)(OR$^1$), each phenyl optionally containing up to three substituents selected from F, Cl, Br, CH$_3$, CF$_3$, CN, OCH$_3$, SCH$_3$; and n represents 0, 1, or 2.

11. A composition of claim 10 wherein R$^2$ represents zero.

12. A composition of claim 10 wherein R$^2$ represents unsubstituted C$_3$–C$_4$ alkyl, optionally substituted benzyl, optionally substituted diphenylmethyl, or CO(C$_1$–C$_4$ alkyl).

13. A composition of claim 12 wherein R$^2$ represents branched chain C$_3$–C$_4$ alkyl.

14. A composition of claim 10 wherein R and R$^1$ each represent methyl.

15. A composition of claim 14 containing the compound O,S-dimethyl ((4-(1,1-dimethylethyl)-1-piperazinyl)carbonyl)phosphoramidothioate.

16. A composition of claim 14 containing the compound O,S-dimethyl ((4-(diphenylmethyl)-1-piperazinyl)carbonyl)phosphoramidothioate.

17. A composition of claim 14 containing the compound O,S-dimethyl ((4-benzyl-1-piperazinyl)carbonyl)phosphoramidothioate.

18. A composition of claim 14 containing the compound O,S-dimethyl ((4-acetyl-1-piperazinyl)carbonyl)phosphoramidothioate.

19. A method of controlling insects which comprises contacting the insects or the locus thereof or the plants on with the insects feed or the locus thereof with an insecticidally effective amount of a compound of the formula

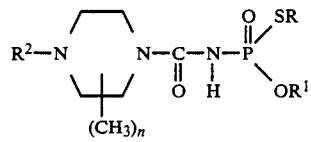

wherein

R and R$^1$ each independently represent C$_1$–C$_4$ alkyl;

R$^2$ represents H, C$_1$–C$_8$ alkyl (optionally containing up to two substituents selected from F, Cl, Br, CN, CO$_2$(C$_1$–C$_4$ alkyl), C$_1$–C$_4$ alkoxy, C$_1$–C4 alkylthio, or phenyl), C$_3$–C$_6$ cycloalkyl, phenyl, COH, CO(C$_1$–C$_4$ alkyl), COphenyl, CO$_2$(C$_1$–C$_4$ alkyl), or CONHP(O)(SR)(OR$^1$), each phenyl optionally containing up to three substituents selected from F, Cl, Br, CH$_3$, CF$_3$, CN, OCH$_3$, SCH$_3$; and n represents 0, 1, or 2.

20. A method of claim 19 wherein n represents zero.

21. A method of claim 19 wherein R$^2$ represents unsubstituted C$_3$–C$_4$ alkyl, optionally substituted benzyl, optionally substituted diphenylmethyl, or CO(C$_1$–C$_4$ alkyl).

22. A method of claim 19 wherein R$^2$ represents branched chain C$_3$–C$_4$ alkyl.

23. A method of claim 19 wherein R and R$^1$ each represent methyl.

24. A method of claim 23 wherein the compound is O,S-dimethyl ((4-(1,1-dimethylethyl)-1-piperazinyl)carbonyl)phosphoramidothioate.

25. A method of claim 23 wherein the compound is O,S-dimethyl ((4-(diphenylmethyl)-1-piperazinyl)carbonyl)phosphoramidothioate.

26. A method of claim 23 wherein the compound is O,S-dimethyl ((4-benzyl-1-piperazinyl)carbonyl)phosphoramidothioate.

27. A method of claim 23 wherein the compound is O,S-dimethyl ((4-acetyl-1-piperazinyl)carbonyl)phosphoramidothioate.

28. A method of claim 19 wherein the insects controlled are sucking insects.

29. A method of claim 28 wherein the insects are leafhoppers.

30. A method of claim 19 wherein the plants are rice plants.

* * * * *

UNITED STATES PATENT AND TRADEMARK OFFICE
CERTIFICATE OF CORRECTION

PATENT NO. : 4,950,657

DATED : August 21, 1990

INVENTOR(S) : W. Reifschneider et al.

It is certified that error appears in the above-identified patent and that said Letters Patent is hereby corrected as shown below:

On the title page, under the heading "Other Publications", for the reference to Derkach et al., *Zh. Obshch. Khim.*, 39, delete "39" and insert -- 33 --;

Col. 6, line 59, delete "C9H18N3O4PS:" and insert -- $C_9H_{18}N_3O_4PS$: --;

Col. 9, line 1, delete "alkyl:" and insert -- alkyl; --;

Col. 9, lines 4 and 5, delete "$C_1$-$C_4$, alkylthio, or phenyl):" and insert -- $C_1$-$C_4$ alkylthio, or phenyl); --;

UNITED STATES PATENT AND TRADEMARK OFFICE
CERTIFICATE OF CORRECTION

PATENT NO. : 4,950,657

DATED : August 21, 1990

INVENTOR(S) : W. Reifschneider et al.

It is certified that error appears in the above-identified patent and that said Letters Patent is hereby corrected as shown below:

Col. 9, line 6, delete "$(C_1 14\ C_4$" and insert -- $(C_1-C_4$ --;

Col. 9, in Claim 11, delete "$R^2$" and insert -- n --.

Signed and Sealed this

Twenty-fifth Day of August, 1992

Attest:

DOUGLAS B. COMER

Attesting Officer

Acting Commissioner of Patents and Trademarks